United States Patent [19]
Larson et al.

[11] Patent Number: 5,613,186
[45] Date of Patent: Mar. 18, 1997

[54] METHOD FOR MONITORING THE ADU PROCESS FOR TECHNETIUM

[75] Inventors: Richard I. Larson; Judith E. Culbreth, both of Wilmington; Juanita H. Pigford, Willard, all of N.C.

[73] Assignee: General Electric Company, Schnectedy, N.Y.

[21] Appl. No.: 584,547

[22] Filed: Jan. 11, 1996

[51] Int. Cl.$^6$ ........................................ C01G 57/00
[52] U.S. Cl. .................................. 423/2; 210/682
[58] Field of Search ............... 423/2, 249; 422/903; 210/682

[56] References Cited

U.S. PATENT DOCUMENTS 5,372,794 12/1994 LeMaire et al. ............................. 423/2
5,458,745 10/1995 Hradil .................................. 204/105 R

OTHER PUBLICATIONS

Q. Chen et al., Analytica Chimica Acta Feb. 1994, 285, 177.

P. R. Makinson, The Comparison of Sample Preparation Techniques . . . , ASTM STP 1291, R. W. Morrow and J. S. Crain, Eds., American Society for Testing and Materials, West Conshohocken, Jun. 1995, pp. 7–19.

T. M. Davis et al., Radioactivity and Radiochemistry Feb. 1993, 4, 14.

E. A. Huff, Spectrochimica Acta Feb. 1987, 42B, 275.

*Primary Examiner*—Ngoclan Mai
*Assistant Examiner*—John R. Hardee
*Attorney, Agent, or Firm*—Nixon & Vanderhye

[57] ABSTRACT

Technetium-99 is quantitatively determined in samples containing uranium using extraction chromatography to remove uranium which otherwise interferes in detecting technetium-99 in low concentrations.

5 Claims, No Drawings

METHOD FOR MONITORING THE ADU PROCESS FOR TECHNETIUM

TECHNICAL FIELD

The presence of technetium-99 is quantitatively determined in a sample containing uranium using extraction chromatography to remove uranium that otherwise interferes in detecting technetium-99 in low concentrations.

BACKGROUND

The world nuclear powers plan to convert nuclear fuel used in the manufacture of weapons to commercial grade $UF_6$ to eliminate weapon grade material and provide energy for peaceful purposes. The fuel will contain other isotopes in small quantities, such as $^{99}Tc$, $^{236}U$, $^{234}U$, etc., due to previous fuel reprocessing, reactor operation, and/or contamination of the enrichment cascades. Consequently, new analytical procedures and experimental techniques must be developed for commercial production of this new type of fuel. An important and integral part of this process is to accurately assay uranium-containing materials to determine levels of technetium as well as other isotopes.

The isotope technetium-99 ($^{99}Tc$) is a fission product that is present in $UF_6$ gas as an impurity, due to its accumulation in the enrichment cascades. Enriched commercial grade $UF_6$ (ECGU) as defined in the ASTM Specification C-996 requires the level of technetium-99 to be less than 0.2 micrograms/gram of $^{235}U$. Technetium-99 originates from spent nuclear fuel that has been reprocessed into $UF_6$ gas. When reprocessed $UF_6$ is fed to the enrichment cascades, technetium-99 accumulates in the upper states. It then becomes an impurity, when non-reprocessed, natural $UF_6$ is fed to the cascades for enrichment purposes.

Prior proposals have not provided rapid and accurate analysis of technetium-99. For example, Morita et al. ("Determination of $^{99}Tc$ in Environmental Samples by Inductively Coupled Plasma Mass Spectrometry", Radiochimica Acta, pp. 63–67, 1993) described an analytical technique using Inductively Coupled Plasma Mass Spectrometry (ICP-MS) to determine Tc-99 in environmental samples. These samples do not contain uranium as an impurity, but ruthenium-99 ($^{99}Ru$) instead. This isotope interferes with the determination of $^{99}Tc$. An involved separation procedure was developed to eliminate the large amount of matrix elements present in these environmental samples. Organic matrix compounds were removed by ashing at 450° C. The inorganic matrix elements were eliminated by coprecipitation with iron hydroxide followed by extraction with TBP-xylene. This was followed by back extraction with NaOH. Tc and ruthenium were then separated from solution by anion exchange. Elution of Tc and ruthenium from the anion exchange resin were accomplished with 8M $NHO_3$. In this process, $^{106}Ru$ could be efficiently separated from technetium by extraction of $^{99}Tc$ With cyclohexanone. Back extraction with carbon tetrachloride and water provided an aqueous solution for ICP-MS analysis. Tc-95 m was used as a tracer to determine the chemical recovery. ICP-MS had a lower detection limit and shorter analytical measurement time when compared with conventional determination methods, which use beta counting.

Alonso, Sena, and Koch ("Determination of $^{99}Tc$ in Nuclear Samples by Inductively Coupled Plasma Mass Spectrometry", Journal of Analytical Atomic Spectrometry, Vol. 9, November 1994) reported that in measuring $^{99}Tc$ with ICP-MS, matrix effects from uranium were not observed at concentrations below 500 µgm/ml. However, Makinson ("The Comparison of Sample Preparation Techniques for Determination of Technetium-99 in Pure Uranium Compounds and Subsequent Analysis by Inductively Coupled Plasma-Mass Spectrometry", a Paper given at the ASTM/DOE conference, October 1994, Gatlinburg, Tenn.) found at 2000 ppm(v), the technetium signal was suppressed 2 to 3 times, while at 5000 ppm(v) the suppression was 10 times that obtained for the technetium solution without uranium. At these uranium concentrations, the ECGU limit of 0.2 µgm/gm $^{235}U$ could not be measured because of technetium peak suppression by uranium.

Our measurements using the ICP-MS showed the suppression of the uranium signal was at least this order of magnitude. Thus, a new analytical procedure was required to determine technetium within a high uranium matrix, such as an ammonium diuranate (ADU) precipitate, uranyl fluoride solution, $UO_2$ powder, and the like. Such a procedure would allow one to monitor the aqueous streams of the ADU process, including the intermediate processing steps and final product.

DISCLOSURE OF THE INVENTION

The analytical procedure of this invention enables monitoring of technetium throughout the entire ammnonium diuranate process from hydrolysis to the waste streams that are eventually released to the environment. This includes the intermediate ammonium diuranate precipitation product as well as the final $UO_2$ product. At concentrations of 2000 µgmU/liter and above, the small concentrations of technetium-99 required by the ECGU limit could not be measured using the inductively coupled plasma mass spectrometer (ICP-MS) using conventional procedures. This was due to the suppression of the technetium peak by uranium. Thus, this procedure was developed that eliminated the uranium interference at these low concentrations of technetium-99.

We have surprisingly discovered that extraction chromatographic columns are capable of extracting and removing the interfering uranium without influencing the recovery of technetium and an accurate quantitative analysis of it. Removal of the uranium prevents suppression of the technetium peak and allows rapid, accurate analysis. Tests using this procedure were used to monitor the ADU process, and showed $^{99}Tc$ to be in the form of the pertechnetate, $TcO_4$ anion. This anion remained in solution throughout the entire process, including the precipitation of ADU from uranyl fluoride solution. Also, a relatively short analytical time was required for this procedure, a few hours, using ICP-MS measurements compared to the conventional procedure of beta counting typically requiring one to two weeks.

Useful information on process performance, product quality ($UO_2$ powder), process upsets, and process waste streams containing uranium were obtained with this method. This analytical procedure can also be applied to other conversion processes, such as steam hydrolysis of $UF_6$, that is, the dry conversion process.

Conventional determination of $^{99}Tc$ using beta counting methods follows the procedure given in ASTM-C761. Separation of Tc is accomplished by liquid extraction with methyl ethyl ketone and stripping the uranium from the solvent with $K_2CO_3$. This procedure required considerable sample preparation time, as well as the time for beta counting.

Described is a method for measuring $^{99}Tc$ using inductively coupled plasma mass spectroscopy including separating uranium from solution in order to accurately measure small quantities of $^{99}Tc$ present in the solution but obscured by the uranium. Technetium can be present in a uranium matrix as a solid, liquid, or gas. As a gas, it accompanies $UF_6$ as $TcF_6$ or $TcO_3F$ which have melting points of 33.4° C. and 18° C., respectively. Hydrolysis of these compounds forms the pertechnetate ion, which is soluble in aqueous solutions. The presence of uranium prevents the analysis of technetium at the required ASTM limits due to suppression of the technetium peak.

The procedure of the present invention allows for the determination of small quantities of technetium by eliminating the presence of uranium prior to analysis for technetium. This is accomplished by removing soluble uranium with a specific extraction chromatographic column.

The process includes the following steps:

1. If a solid, dissolve the sample in nitric acid,
2. If a liquid, determine the total uranium concentration,
3. optionally dilute the sample to a concentration of about 6000 ppm.
4. pass the sample through an extraction column to remove uranium leaving technetium in the effluent,
5. rinse the column to remove any residual technetium on the column with dilute nitric acid, if necessary,
6. in the effluent from steps 4 and 5, oxidize the technetium with hydrogen peroxide or other suitable oxidizer to form the pertechnetate ($TcO_4^-$) ion,
7. pass the pertechnetate-containing solution from step 6 through an extraction chromatographic column to selectively sorb and extract the technetium, then
8. strip the column used in step 7 to remove the technetium. The prepared sample is now ready for analysis.

BEST MODE FOR CARRYING OUT THE INVENTION

Technetium-containing samples also containing significant uranium concentrations were analyzed using the above procedure. Extraction chromatographic columns were prepared and the analysis was conducted as follows:

Condensing columns that separate uranium from the test solution: Load column with resin to extract the uranium at an amount of 1 gram of resin per 0.7 gram of uranium. Condition each column (UTEVA Spec, EiChrom Industries) with 10 ml of 2N nitric acid and allow it to drain. Transfer each test solution to a column and allow it to drain into an acid cleaned beaker. Rinse each column with two 5 ml portions of 2N nitric and drain into the same beaker. To each beaker containing the collected drainings from the column, add 10 ml of 30% $H_2O_2$, stir, cover and heat at about 90° C. for one hour to oxidize the Tc to Tc(VII) to form the pertechnetate. If necessary, continue heating until bubbling stops. Allow the beakers to cool to room temperature.

Conditioning the columns to determine the technetium concentration: for each sample, place a TEVA-SPEC (EiChrom Industries) prepackaged column in a rack. Remove the bottom plug and allow the column to drain. Pipette 5 ml of 0.1N nitric acid into each column to condition the resin and allow it to drain. Transfer each sample from which the uranium has been removed, as prepared above, to a column and allow to drain. Rinse the original beaker with two 5 ml portions of DIW and transfer each rinse to the column. Pipette 25 ml of 1N nitric acid directly into each column and allow to drain. Discard all drainings. Place a clean beaker below each column. Pipete 20 ml of 4N nitric acid into each column to elute the Tc. Allow it to drain into the beaker, then heat the beaker gently, not above 80° C., until the volume is about 5 ml. Transfer the solution to a small graduated plastic centfifuge tube. Add the Y internal standard to each tube. Add two 2 ml volumes of water to each beaker and transfer each rinse solution to the tube, such that the final concentration of Y is 20 ng/ml. Make up to a final volume of 10 ml with DIW, then measure Tc-99 and Ru-102 by ICP-MS using standards in the range 0.005 to 0.1 ng/ml.

Using a $^{99}Tc$ standard at 1.15 µgm/ml, a calibration curve for the ICP-MS is established at technetium concentrations of 0.005, 0.010, 0.025, 0.05, and 0.1 ηg/ml. The technetium concentration for samples prepared as outlined above are determined using this calibration curve, and by the ICP-MS intensities at m/z of 99.

This technetium analysis was performed on samples taken throughout the ADU process including uranyl fluoride solution formed during the hydrolysis of $UF_6$; wet ADU precipitate formed on the reaction of uranyl fluoride solution with ammonia; liquid leaving the ADU precipitation process following centrifugation and clarification (high speed centrifugation); and scrubber water of gases leaving the calciner. The ADU precipitate following centrifugation and clarification is fed to the calciner. Technetium on entering the calciner would vaporize and be removed by the scrubber.

Technetium in the form of pertechnetate anion ($TcO_4^-$) is likely to be found in the samples obtained from the uranyl fluoride solution and liquid leaving the ADU process. The wet ADU precipitate and scrubber water are not expected to contain technetium. Samples from the above ADU processing locations were analyzed by beta counting after liquid extraction of uranium and other isotopes for comparison purposes, and the ICP-MS procedure of the present invention. The results are shown below.

| Uranyl Fluoride Solutions | |
|---|---|
| ICP-MS µgm/gm$^{235}$U | Beta Counting µgm/gm$^{235}$U |
| 0.22 | 0.24 |
| 0.18 | 0.23 |
| 0.20 | 0.22 |
| 0.26 | 0.30 |
| 0.31 | 0.30 |
| 0.40 | 0.40 |
| 0.71 | 0.69 |

| Calciner Scrubber Water | |
|---|---|
| ICP-MS ηgm/ml | Beta Counting ηgl/ml |
| <0.0016 | <0.003 |
| <0.0016 | <0.003 |

| ADU Precipitate | |
|---|---|
| ICP-MS µgm/gm (wet ADU) | Beta Counting µgm/gm (wet ADU) |
| <0.005 | <1.0 |
| <0.007 | <1.0 |

| Liquid Leaving ADU Precipitation | |
|---|---|
| ICP-MS ηgl/ml | Beta Counting ηgl/ml |
| 0.005 | <0.003 |
| 0.23 | 0.18 |

| $UO_2$ Powder | |
|---|---|
| ICP-MS µgm/gm$^{235}$U | Beta Counting µgm/gm$^{235}$U |
| <0.042 | <0.005 |

These results show reasonable even impressive agreement between the conventional ASTM beta counting procedure and the results of the present invention. Tests with a known $^{99}$Tc standard show 96% recovery using this procedure. Technetium was not found in the ADU precipitate, $UO_2$ powder, and calciner scrubber water. This indicates the presence of soluble pertechnetate throughout the ADU process.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A process of determining the presence of technetium-99 in a sample containing uranium comprising the steps of sequentially:

(a) solubilizing the uranium contained in the sample;

(b) selectively removing the solubilized uranium from the sample;

(c) solubilizing the technetium-99 in the sample by converting it to the pertechnetate ion form;

(d) selectively sorbing the pertechnetate ions on an extraction chromatographic column;

(e) eluting the sorbed technetium-99 from the extraction chromatographic column; and (f) determining the amount of technetium-99 contained in the eluant of step (e).

2. The process of claim 1 wherein the sample is solubilized in step (a) with nitric acid.

3. The process of claim 1 wherein the solubilized uranium is removed in step (b) by sorption on an extraction chromatographic column.

4. The process of claim 1 wherein the technetium-99 is solubilized in step (c) with a peroxide.

5. The process of claim 1 wherein the column is eluted in step (e) with nitric acid.

* * * * *